US010449101B2

(12) United States Patent
Brosnan et al.

(10) Patent No.: US 10,449,101 B2
(45) Date of Patent: Oct. 22, 2019

(54) PATIENT SUPPORT APPARATUS AND METHODS FOR SUPPLYING FEEDBACK TO A USER

(71) Applicant: Stryker Corporation, Kalamazoo, MI (US)

(72) Inventors: Daniel V. Brosnan, Kalamazoo, MI (US); Aaron Douglas Furman, Kalamazoo, MI (US); Janani Gopalkrishnan, Portage, MI (US)

(73) Assignee: STRYKER CORPORATION, Kalamazoo, MI (US)

( * ) Notice: Subject to any disclaimer, the term of this patent is extended or adjusted under 35 U.S.C. 154(b) by 0 days.

(21) Appl. No.: 15/854,997

(22) Filed: Dec. 27, 2017

(65) Prior Publication Data

US 2018/0185220 A1 Jul. 5, 2018

Related U.S. Application Data

(60) Provisional application No. 62/440,141, filed on Dec. 29, 2016.

(51) Int. Cl.
*G08B 6/00* (2006.01)
*G09B 21/00* (2006.01)
(Continued)

(52) U.S. Cl.
CPC ............ *A61G 7/018* (2013.01); *A61G 7/012* (2013.01); *A61G 7/015* (2013.01); *A61G 7/0506* (2013.01);
(Continued)

(58) Field of Classification Search
CPC ...... A61G 7/018; A61G 7/0524; A61G 7/015; A61G 7/0506; A61G 7/0514; A61G 7/012;
(Continued)

(56) References Cited

U.S. PATENT DOCUMENTS 7,888,901 B2 2/2011 Larson et al.
8,131,321 B2 3/2012 Linjama et al.
(Continued)

FOREIGN PATENT DOCUMENTS

WO 2017045144 A1 3/2017

OTHER PUBLICATIONS

Stryker, "TrueRize Clinical Chair", Mkt Lit-1225, Nov. 16, 2015, Rev A.2; 4 pages.

*Primary Examiner* — Tanmay K Shah
(74) *Attorney, Agent, or Firm* — Howard & Howard Attorneys PLLC (57) ABSTRACT

A patient support apparatus comprising a support structure, an input device, an actuator, and a controller. The support surface comprises a patient support surface. The input device generates an input signal. The actuator is coupled to the support structure and is configured to perform an operational function and a feedback function, separate from the operational function, to provide feedback to a user. The controller is in communication with the actuator and the input device and is configured to control the actuator to perform the operational function in response to receiving the input signal from the input device, and to control the actuator to perform the feedback function separate from performing the operational function.

25 Claims, 9 Drawing Sheets (51) Int. Cl.
| | |
|---|---|
| H04B 3/36 | (2006.01) |
| A61G 7/018 | (2006.01) |
| H02K 1/27 | (2006.01) |
| H02K 1/16 | (2006.01) |
| H02K 41/03 | (2006.01) |
| H02K 7/14 | (2006.01) |
| G06F 3/01 | (2006.01) |
| H02K 21/14 | (2006.01) |
| A61G 7/012 | (2006.01) |
| H02K 1/14 | (2006.01) |
| A61G 7/015 | (2006.01) |
| A61G 7/05 | (2006.01) |
| A61G 7/008 | (2006.01) |
| A61G 7/00 | (2006.01) |
| A61G 7/053 | (2006.01) |
| A47B 23/02 | (2006.01) |
| H02K 11/215 | (2016.01) |
| A61B 5/11 | (2006.01) |

(52) U.S. Cl.
CPC .......... *A61G 7/0514* (2016.11); *A61G 7/0524* (2016.11); *G06F 3/016* (2013.01); *H02K 1/146* (2013.01); *H02K 1/16* (2013.01); *H02K 1/2733* (2013.01); *H02K 1/2753* (2013.01); *H02K 7/14* (2013.01); *H02K 21/14* (2013.01); *H02K 41/031* (2013.01); *A47B 23/025* (2013.01); *A61B 5/1115* (2013.01); *A61G 7/001* (2013.01); *A61G 7/008* (2013.01); *A61G 7/053* (2013.01); *A61G 2203/10* (2013.01); *A61G 2203/32* (2013.01); *A61G 2203/34* (2013.01); *A61G 2203/36* (2013.01); *A61G 2203/38* (2013.01); *A61G 2203/42* (2013.01); *A61G 2203/46* (2013.01); *H02K 11/215* (2016.01)

(58) Field of Classification Search
CPC .. A61G 2203/32; H02K 1/2733; H02K 1/146; H02K 21/14; H02K 41/031; H02K 1/16; H02K 1/2753; H02K 7/14; G06F 3/016
USPC ...................................................... 340/407.2
See application file for complete search history.

(56) References Cited

U.S. PATENT DOCUMENTS

| | | |
|---|---|---|
| 8,141,947 B2 | 3/2012 | Nathan et al. |
| 8,179,060 B2 | 5/2012 | Wende et al. |
| 8,896,524 B2 | 11/2014 | Birnbaum et al. |
| 2009/0100599 A1 | 4/2009 | Rawls-Meehan |
| 2012/0119886 A1* | 5/2012 | Rawls-Meehan .... A47C 20/041 340/12.5 |
| 2016/0331617 A1 | 11/2016 | Stryker et al. |
| 2016/0349854 A1 | 12/2016 | Hayes et al. |
| 2017/0149365 A1 | 5/2017 | Burger |
| 2017/0245555 A1* | 8/2017 | Karp ...................... A41B 13/06 |

* cited by examiner

PATIENT SUPPORT APPARATUS AND METHODS FOR SUPPLYING FEEDBACK TO A USER

RELATED APPLICATION

This application claims priority to and the benefit of U.S. Provisional Patent Application No. 62/440,141, filed on Dec. 29, 2016, the entire contents and disclosure of which are hereby incorporated herein by reference.

BACKGROUND

Patient support apparatuses, such as hospital beds, stretchers, cots, tables, wheelchairs, and chairs are used to help facilitate care of patients in a health care setting. Conventional patient support apparatuses generally comprise a base and a patient support surface upon which the patient is supported. Often, these patient support apparatuses have one or more powered devices with motors to perform one or more functions, such as lifting and lowering the patient support surface, articulating one or more deck sections, raising a patient from a slouched position, turning a patient, centering a patient, extending a length or width of the patient support apparatus, and the like.

When the caregiver wishes to operate a powered device to perform a function, the caregiver actuates a user input device of a user interface, often in the form of a button on a control panel. In certain applications, the button is realized as a physical, movable component that is configured to be depressed, switched, toggled, and the like to actuate the powered device. Here, physical movement of the button provides tactile feedback to the caregiver when the caregiver actuates the button. In other applications, the "button" of the user input device may be realized in connection with a touchscreen. Here, conventional touchscreens, as well as other types of input devices, do not provide tactile feedback to the caregiver. In these cases, separate feedback devices may be provided to provide the caregiver with a form of tactile feedback to indicate that the "button" of the touchscreen has been properly actuated. For example, motors which rotate an object with a center of mass offset from the axis of rotation may be employed by or in cooperation with the touchscreen to provide tactile feedback in the form of vibration. However, the use of such motors can add cost and complexity to the touchscreen and, thus, to the patient support apparatus. Similarly, in the event that an alarm needs to be sounded (for example, to alert the caregiver when the patient attempts to exit the patient support apparatus unattended), separate annunciators are employed to output the alarm (for example, speakers). Here too, additional components associated with alarms can add cost and complexity to the patient support apparatus.

While patient support apparatuses have generally performed well for their intended purpose, there remains a need in the art for a patient support apparatus which overcomes the disadvantages in the prior art.

DETAILED DESCRIPTION

Figure 1:
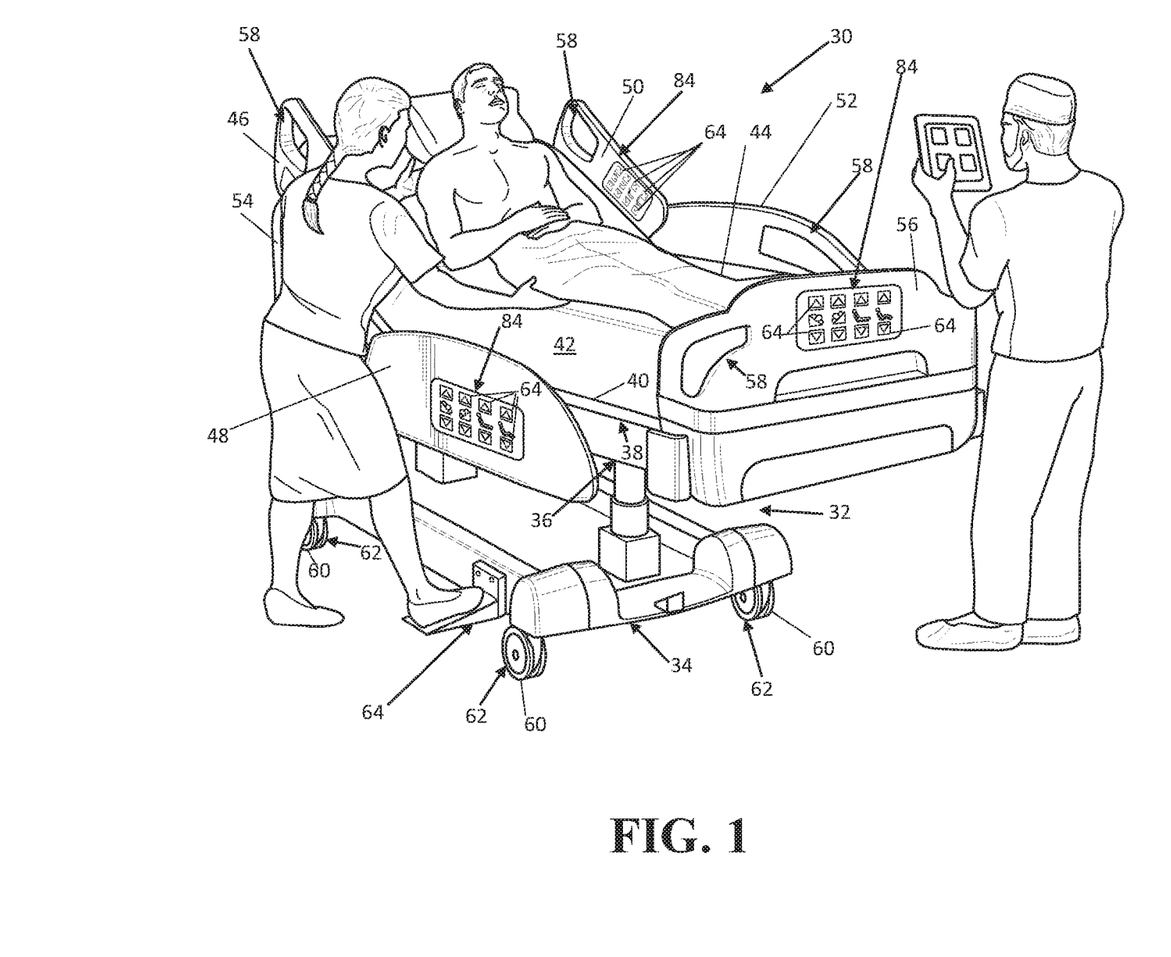
FIG. 1 is perspective view of a patient support apparatus.

Referring to FIG. 1, a patient support apparatus 30 is shown for supporting a patient in a health care setting. The patient support apparatus 30 illustrated in FIG. 1 is realized as a hospital bed. In other embodiments, however, the patient support apparatus 30 may be a stretcher, cot, table, wheelchair, chair, or similar apparatus utilized in the care of a patient.

A support structure 32 provides support for the patient. The support structure 32 illustrated in FIG. 1 comprises a base 34 and an intermediate frame 36. The intermediate frame 36 is spaced above the base 34. The support structure 32 also comprises a patient support deck 38 disposed on the intermediate frame 36. The patient support deck 38 comprises several sections, some of which articulate relative to the intermediate frame 36, such as a fowler section, a seat section, a thigh section, and a foot section. The patient support deck 38 provides a patient support surface 40 upon which the patient is supported.

A mattress 42 is disposed on the patient support deck 38. The mattress 42 comprises a secondary patient support surface 44 upon which the patient is supported. The base 34, intermediate frame 36, patient support deck 38, and patient support surfaces 40, 44 each have a head end and a foot end corresponding to designated placement of the patient's head and feet on the patient support apparatus 30. The construction of the support structure 32 may take on any known or conventional design, and is not limited to that specifically set forth above. In addition, the mattress 42 may be omitted in certain embodiments, such that the patient rests directly on the patient support surface 40.

Side rails 46, 48, 50, 52 are coupled to the intermediate frame 36 and thereby supported by the base 34. A first side rail 46 is positioned at a right head end of the intermediate frame 36. A second side rail 48 is positioned at a right foot end of the intermediate frame 36. A third side rail 50 is positioned at a left head end of the intermediate frame 36. A fourth side rail 52 is positioned at a left foot end of the intermediate frame 36. If the patient support apparatus 30 is a stretcher or a cot, there may be fewer side rails. The side rails 46, 48, 50, 52 are movable between a raised position in which they block ingress and egress into and out of the patient support apparatus 30, one or more intermediate positions, and a lowered position in which they are not an obstacle to such ingress and egress. In still other configurations, the patient support apparatus 30 may not include any side rails.

A headboard 54 and a footboard 56 are coupled to the intermediate frame 36. In other embodiments, when the headboard 54 and footboard 56 are included, the headboard 54 and footboard 56 may be coupled to other locations on the patient support apparatus 30, such as the base 34. In still other embodiments, the patient support apparatus 30 does not include the headboard 54 and/or the footboard 56.

Caregiver interfaces 58, such as handles, are shown integrated into the footboard 56 and side rails 46, 48, 50, 52 to facilitate movement of the patient support apparatus 30 over floor surfaces. Additional caregiver interfaces 58 may be integrated into the headboard 54 and/or other components of the patient support apparatus 30. The caregiver interfaces 58 are graspable by the caregiver to manipulate the patient support apparatus 30 for movement.

Other forms of the caregiver interface 58 are also contemplated. The caregiver interface 58 may comprise one or more handles coupled to the intermediate frame 36. The caregiver interface may simply be a surface on the patient support apparatus 30 upon which the caregiver logically applies force to cause movement of the patient support apparatus 30 in one or more directions, also referred to as a push location. This may comprise one or more surfaces on the intermediate frame 36 or base 34. This could also comprise one or more surfaces on or adjacent to the headboard 54, footboard 56, and/or side rails 46, 48, 50, 52. In other embodiments, the caregiver interface may comprise separate handles for each hand of the caregiver. For example, the caregiver interface may comprise two handles.

With continued reference to FIG. 1, wheels 60 are coupled to the base 34 to facilitate transport over the floor surfaces. The wheels 60 are arranged in each of four quadrants of the base 34 adjacent to corners of the base 34. In the embodiment shown, the wheels 60 are caster wheels able to rotate and swivel relative to the support structure 32 during transport. Each of the wheels 60 forms part of a caster assembly 62. Each caster assembly 62 is mounted to the base 34. It should be understood that various configurations of the caster assemblies 62 are contemplated. In addition, in some embodiments, the wheels 60 are not caster wheels and may be non-steerable, steerable, non-powered, powered, or combinations thereof. Additional wheels are also contemplated. For example, the patient support apparatus 30 may comprise four non-powered, non-steerable wheels, along with one or more powered wheels. In some cases, the patient support apparatus 30 may not include any wheels.

In other embodiments, one or more auxiliary wheels (powered or non-powered), which are movable between stowed positions and deployed positions, may be coupled to the support structure 32. In some cases, when these auxiliary wheels are located between caster assemblies 62 and contact the floor surface in the deployed position, they cause two of the caster assemblies 62 to be lifted off the floor surface thereby shortening a wheel base of the patient support apparatus 30. A fifth wheel may also be arranged substantially in a center of the base 34.

Referring now to FIGS. 1-3D, the patient support apparatus 30 further comprises an input device 64, an actuator 66, and a controller 68. The input device 64 is configured to generate an input signal IS (see FIGS. 3A-3D). The actuator 66 is coupled to the support structure 32 and is configured to independently perform an operational function OF (see FIG. 3A) and a feedback function FF (see FIGS. 3B-3D). More specifically, the actuator 66 is configured to perform the feedback function FF separate from the operational function OF. As is described in greater detail below, the feedback function FF provides feedback FB to a user, such as the caregiver, the patient, and the like. The controller 68 is in communication with the actuator 66 and the input device 64, and is configured to control the actuator 66 to perform the operational function OF in response to receiving the input signal IS from the input device 64, and to control the actuator 66 to perform the feedback function FF separate from performing the operational function OF. The input device, actuator 66, and controller 68 will each be described in greater detail below.

The patient support apparatus 30 may comprise one or more powered devices 70 each coupled to the support structure 32 and having one or more actuators 66 configured to perform one or more operational functions OF. To this end, the patient support apparatus could employ a battery and/or external power (not shown) to supply energy to the powered devices 70, the controller 68, the actuators 66, the input device 64, and the like.

Figure 2:
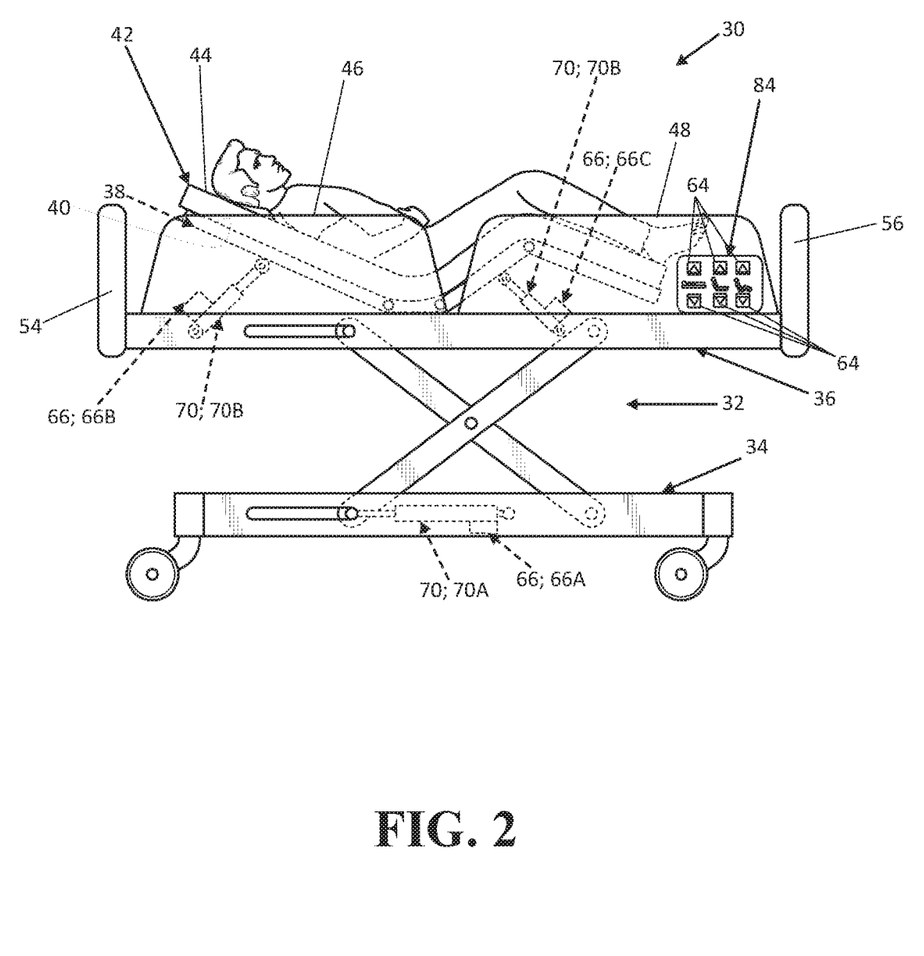
FIG. 2 is a side view of another patient support apparatus shown having input devices, a support structure having a patient support deck spaced above a base, an actuator arranged to move the patient support deck relative to the base, and actuators arranged to move sections of the patient support deck.
Figure 3A:
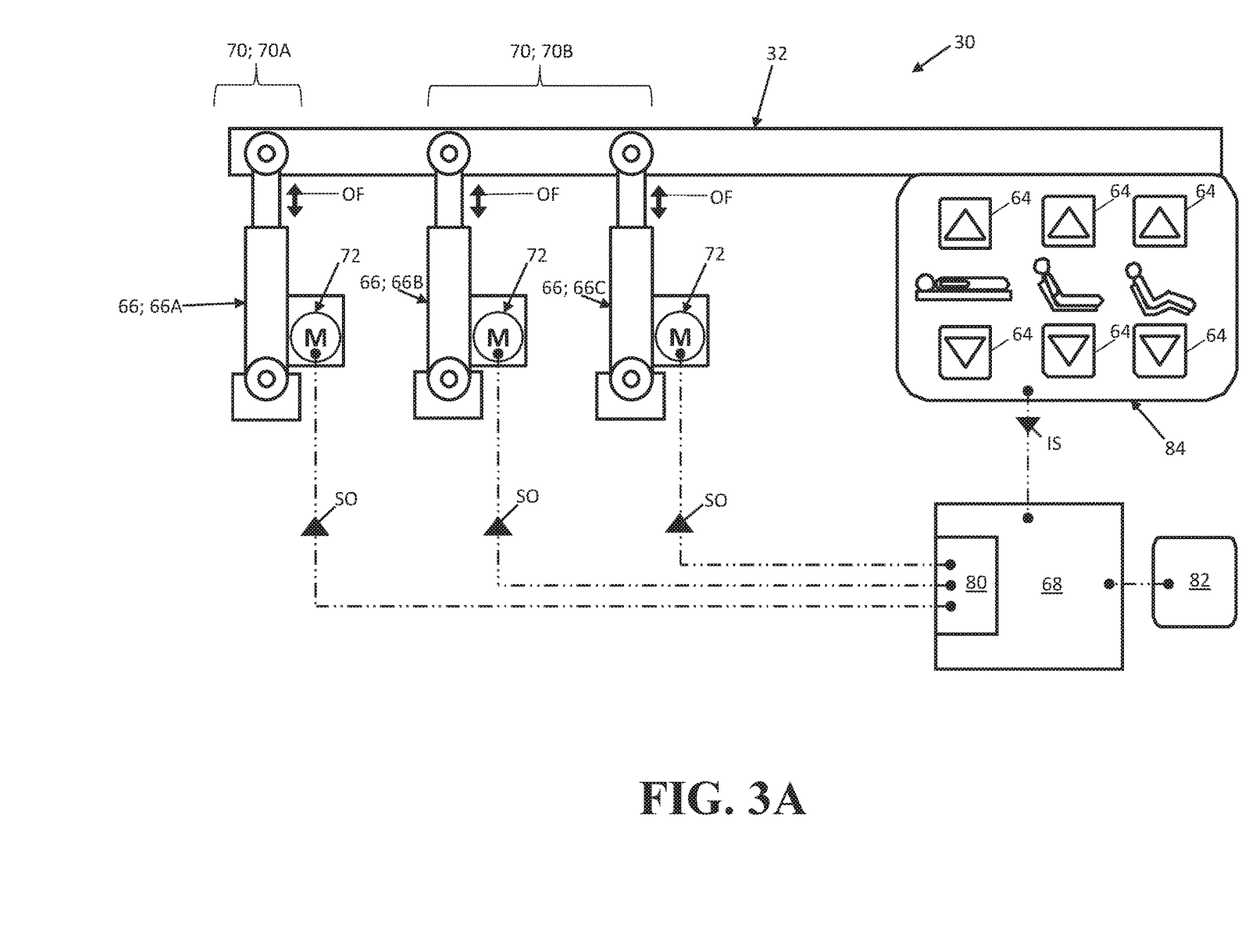
FIG. 3A is a illustrated view of a control system of a patient support apparatus, depicted with a controller disposed in communication with input devices and actuators operatively attached to a support structure, the actuators each being configured to perform an operational function.
Figure 3B:
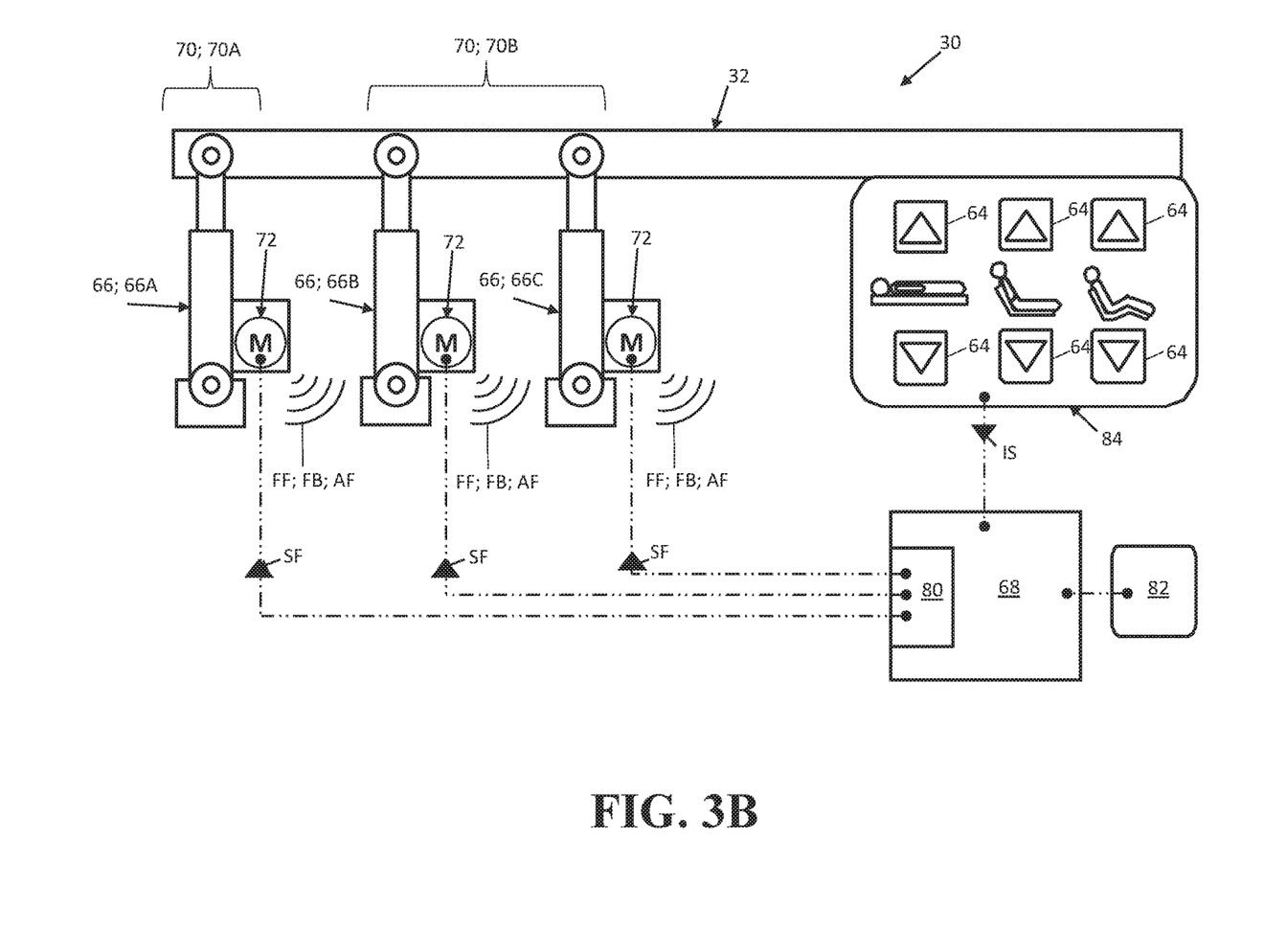
FIG. 3B is another illustrative view of the control system of FIG. 3A, with the actuators each being configured to perform a feedback function realized as audible feedback, the feedback functions shown performed independent of the operational functions illustrated in FIG. 3A.
Figure 3C:
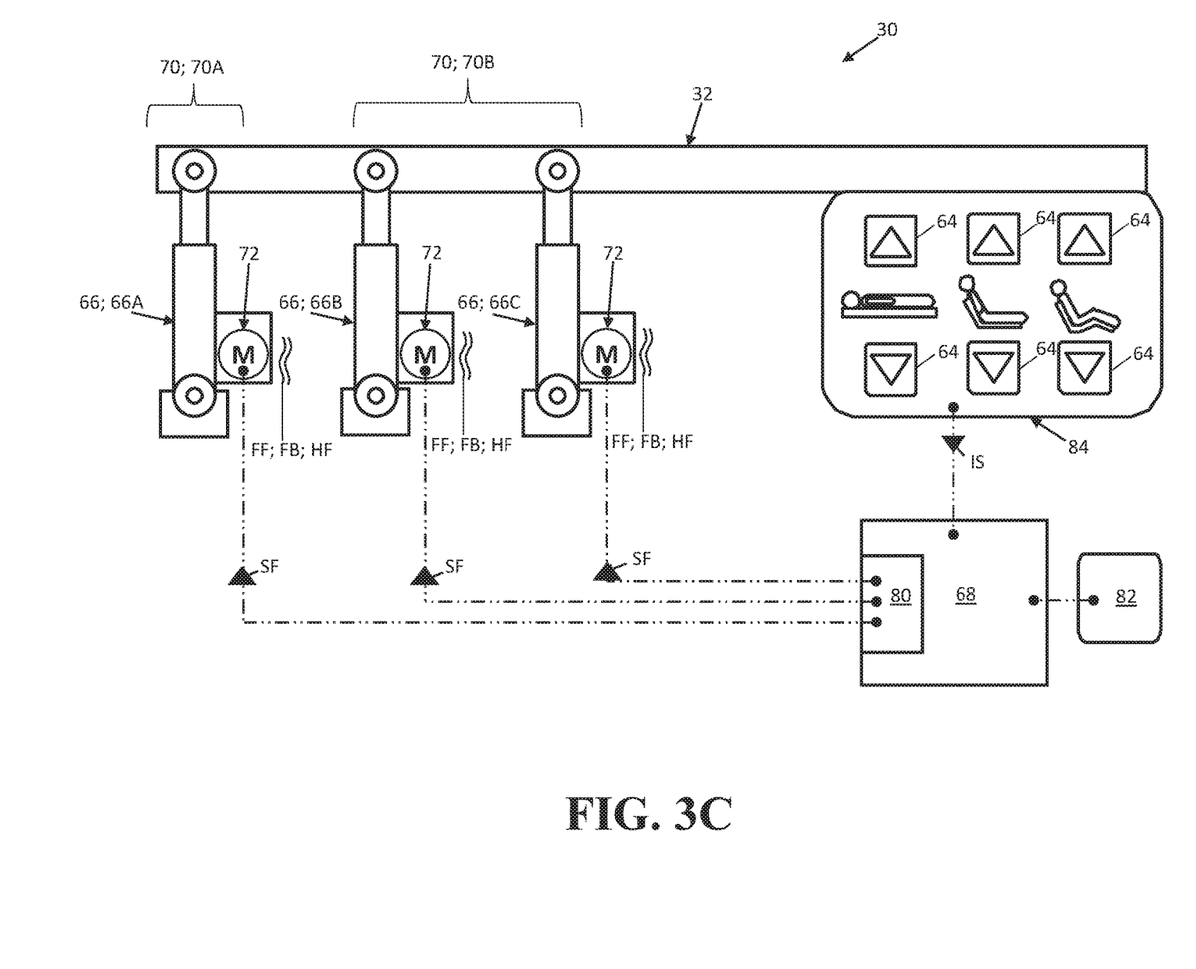
FIG. 3C is another illustrative view of the control system of FIGS. 3A-3B, with the actuators each being configured to perform a feedback function realized as vibrational haptic feedback generation, the feedback functions shown performed independent of the operational functions illustrated in FIG. 3A.
Figure 3D:
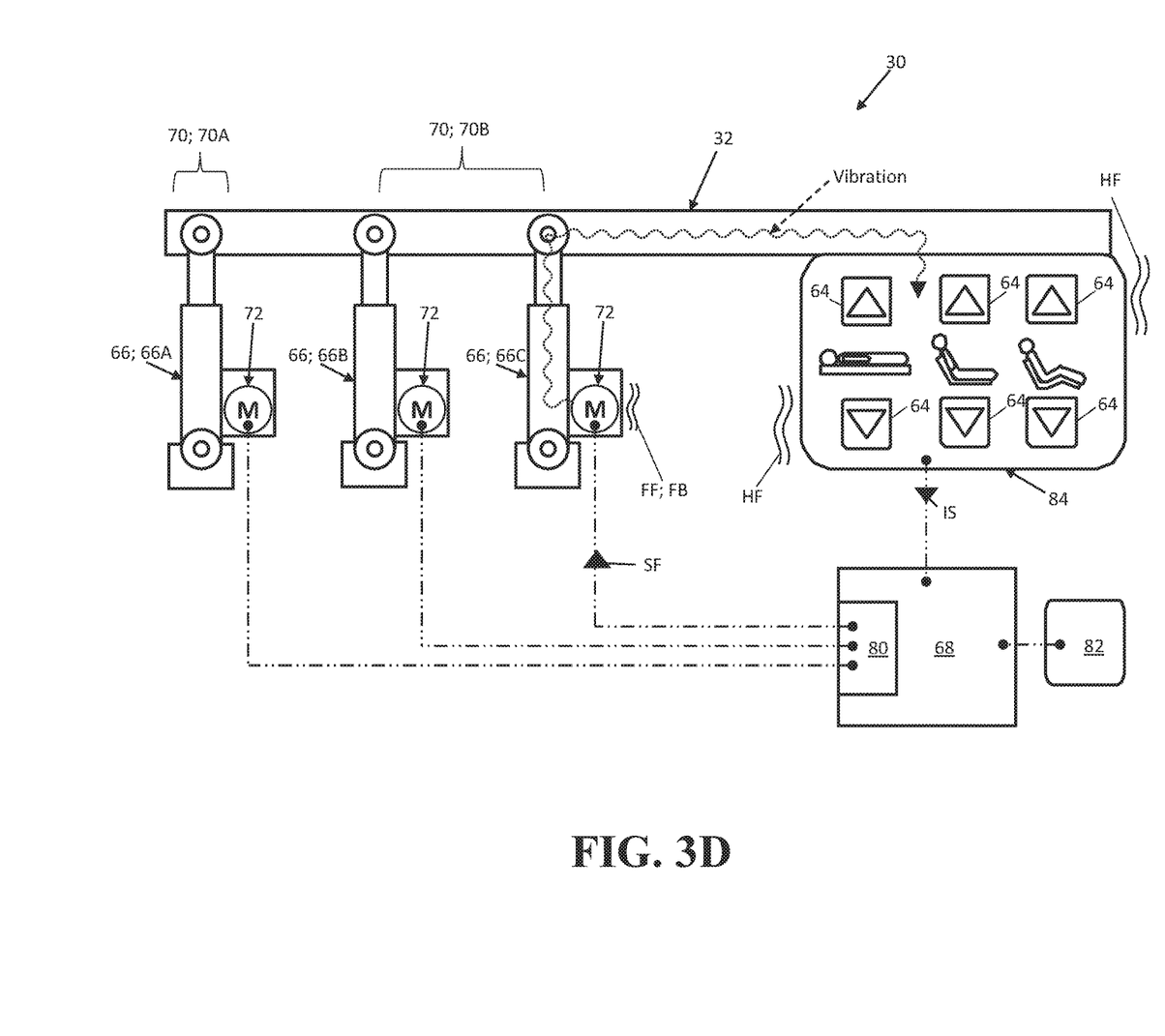
FIG. 3D is another illustrative view of the control system of FIGS. 3A-3C, with one of the actuators shown generating vibrational haptic feedback translated through the support structure to the input device.

In the representative embodiment illustrated in FIGS. 2-3D, the patient support apparatus is shown with two powered devices 70: a lift device, generally indicated at 70A, and a deck adjustment device 70B. Here, the lift device 70A employs a lift actuator 66A arranged in force-translating relationship between the base 34 and the intermediate frame 36 to move the patient support deck 38 relative to the base 34. Thus, the lift actuator 66A performs the operational functions OF of raising and lowering the patient support deck 38. Put differently, the operational function OF performed by the lift actuator 66A may be further defined as a first movement function to move a first portion of the support structure 32 (the patient support deck 38). Here too in this embodiment, the deck adjustment device 70B employs a first deck actuator 66B and a second deck actuator 66C arranged in force-translating relationship between the intermediate frame 36 and respective sections of the patient support deck 38 to articulate, move, or otherwise position the sections of the patient support deck 38 relative to each other and to the intermediate frame 36. Thus, the deck actuators 66B, 66C each perform the operational functions OF of moving sections of the patient support deck 38. Put differently, the operational functions OF performed by the deck actuators 66B, 66C may be further defined as second movement functions to move a second portion of the support structure 32 (the sections of the patient support deck 32).

As noted above, the lift actuator 66A, the first deck actuator 66B, and the second deck actuator 66C are each coupled to the support structure 32 and are configured to perform both an operational function OF and to perform a feedback function FF to provide feedback FB to the user, as noted above and as is described in greater detail below. While the representative embodiment of the patient support apparatus 30 illustrated throughout the drawings and described herein employs powered devices 70 realized as the lift device 70A and the deck adjustment device 70B, those having ordinary skill in the art will appreciate that other suitable types of powered devices 70 which employ actuators 66 configured to independently perform operational functions OF and feedback functions FF could be implemented into the patient support apparatus 30. By way of non-limiting example, other suitable powered devices may further be implemented into the patient support apparatus 30 as: a drive device to propel the patient support apparatus 30; a patient centering device to center the patient on the patient support surface 40, 44; a patient turning device to turn the patient on the patient support surface 40, 44; a patient ingress/egress device to limit/allow patient ingress/egress to/from the patient support deck 38; a bed length extension device to adjust the length of the patient support apparatus 30; a bed width extension device to adjust the width of the patient support apparatus 30. The Applicant has described such powered devices in U.S. Patent Application Pub. No. 2017/0143565, filed Nov. 16, 2016, entitled, "Patient Support Systems and Methods for Assisting Caregivers with Patient Care," which is hereby incorporated by reference in its entirety.

Figure 4:
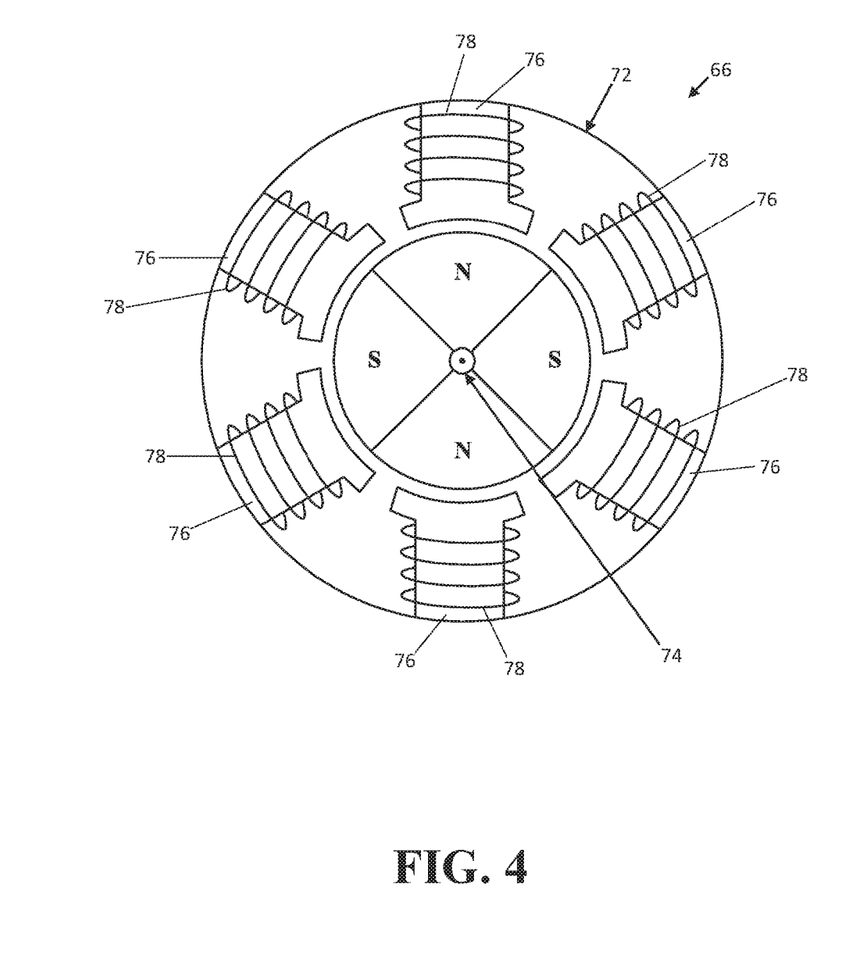
FIG. 4 is a schematic view of a brushless electric motor employed by the actuators of FIGS. 3A-3D, according to one embodiment.

Referring now to FIGS. 3A-4, the lift actuator 66A and the first and second deck actuators 66B, 66C are each realized as linear actuators which comprise motors, generally indicated at 72, to drive the respective actuators 66 to perform respective operational functions OF and to perform respective feedback functions FF to generate feedback FB. To this end, in the representative embodiment illustrated herein, the motor 72 of each actuator 66 is realized a brushless electric motor 72 disposed in communication with and driven by the controller 68. As is shown in FIG. 4, the motor 72 has an internal rotor 74 and an external stator 76 with a plurality of windings or coils 78, which are in spaced radial arrangement with the rotor 74 and which are disposed in electrical communication with the controller 68. However, it will be appreciated that the motor 72 could be of any suitable type or configuration sufficient to perform operational and feedback functions OF, FF noted above. By way of non-limiting example, the motor 72 could be a brushed electric motor. It will be appreciated that a single motor 72, or more than one motor 72, could be used to generate the feedback FB to perform the feedback function FF. Similarly, a single motor 72 could be used to perform certain feedback functions FF, and a different motor 72 could be used to perform other feedback functions FF.

Moreover, as will be appreciated from the subsequent description below, any one of the actuators 66 could be realized in a number of different ways, and from a number of different components which cooperate to perform operational and feedback functions OF, FF noted above. By way of non-limiting example, one or more of the actuators 66 could be realized as a pump assembly disposed in fluid communication with valves arranged to control a pneumatic or hydraulic linear or rotary actuator (not shown). Thus, those having ordinary skill in the art will appreciate that each actuator 66A, 66B, 66C could be of a different type or configuration. In one embodiment, the controller 68 comprises a drive circuit 80 configured to generate one or more output signals, waveforms, and the like to drive the motor 72 and to provide the feedback FB. Here, it will be appreciated that a single waveform or output signal could be employed both to drive the motor 72 and to provide the feedback FB, separate waveforms or output signals could be employed to respectively drive the motor 72 and to provide the feedback FB, or discrete portions of a common waveform or output signal could respectively drive the motor 72 and provide the feedback FB. In one embodiment, the output signal is a pulse-width modulation signal. However, the output signal could be of any suitable type or configuration sufficient to drive the motor 72 and to provide the feedback FB, as noted above.

In one embodiment, the controller 68 independently generates an operate signal SO to drive the motor 72 to perform the operational function OF (see FIG. 3A), and a feedback signal SF to drive the motor 72 to perform the feedback function FF (see FIGS. 3B-3D). Here, the operate signal SO could be of any suitable configuration (e.g., duty cycle, frequency, voltage, etc.) sufficient to effect generation of rotational torque by the motor 72, whereas the feedback signal SF could be of any suitable configuration (e.g., duty cycle, frequency, voltage, etc.) sufficient to effect generation of feedback FB by the motor 72 without effecting generation of rotational torque needed to perform its operational function OF. More specifically, where the motor 72 is a brushless electric motor, the operate signal SO could have suitable motor parameters (e.g., duty cycle, frequency, voltage, etc.) to commutate the motor 72 and subsequently drive the motor 72 to generate rotational torque by causing rotation of the rotor 74 relative to the stator 76 to effect the operational function OF, and the feedback signal SF could have motor parameters (e.g., duty cycle, frequency, voltage, etc.) that is insufficient to commutate the motor 72 in the same manner, but sufficient to generate feedback FB by the motor 72 to effect the feedback function FF. Here, the feedback signal SF could move the rotor 74 back-and-forth between adjacent coils 78, thereby preventing commutated, full rotation (e.g., 360 degrees) of the rotor 74 while, at the same time, causing the motor 72 to vibrate to generate the feedback FB.

Depending on the frequency with which the feedback signal SF causes the rotor 74 of the motor 72 to vibrate, the resulting feedback FB generated by the motor 72 could be audible feedback AF and/or haptic feedback HF, each of which will be described in greater detail below. In one version, the drive circuit 80 generates a digital signal, such as a pulse-width modulation (PWM) signal at a suitable duty cycle and frequency that, when applied to the motor 72, causes the motor 72 to vibrate in the audible range for humans (e.g., from 20 Hz to 20 kHz), but without overcoming friction and any load on the motor shaft (e.g., rotor 74) to cause full rotation. In other words, the rotor 74 rotates less than 360 degrees, less than 180 degrees, and/or less than 120 degrees when operating to generate feedback FB, whereas the rotor 74 may rotate 360 degrees or more when performing the operational function OF. Thus, the feedback function can be performed separately from the operational function by varying motor parameters (e.g., power parameters) applied to the motor 72, such as varying the duty cycle, frequency, voltage, etc. In some cases, the duty cycle may be selected so that the motor 72 is turned on, stalls, then turns off, with this cycle being continuously repeated making the motor 72 vibrate at the PWM frequency, which may be in the audible range for humans. In some cases, the rotor 74 is rotatably supported by a casing of the motor 72 such that vibrations of the rotor 74 are transmitted to the casing and/or to other components of the patient support apparatus 30 to which the motor 72 is attached.

Figure 4A:
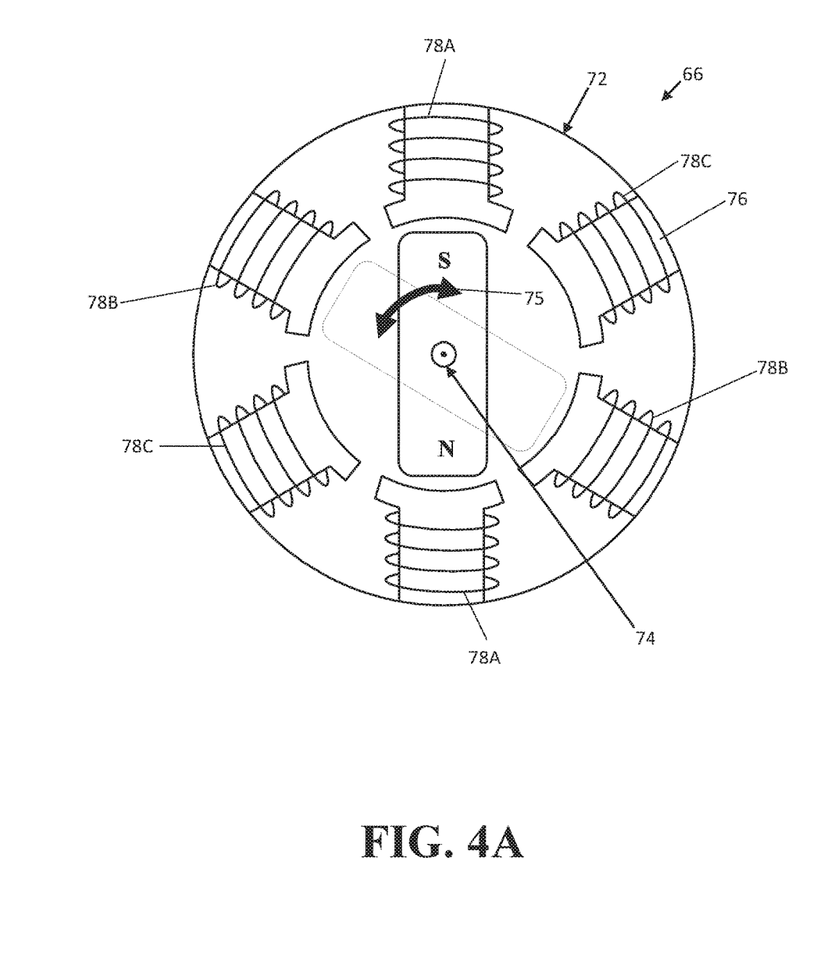
FIG. 4A is a schematic view of another brushless electric motor employed by the actuators of FIGS. 3A-3D, according to one embodiment.

In one version shown in FIG. 4A, the motor 72 may comprise a three-phase brushless DC motor in which the controller 68 energizes three sets of windings 78A, 78B, 78C in sequence to generate a variable magnetic field so that the rotor 74 rotates to perform the operational function OF, e.g., by fully rotating clockwise or counterclockwise. Conversely, to provide the feedback function FF, the controller 68 may: energize only one set of the windings 78A, 78B, 78C; energize only two sets of the windings 78A, 78B, 78C;

or may energize all the windings 78A, 78B, 78C in a manner that causes the rotor 74 to oscillate back-and-forth, and thus vibrate. For example, the rotor 74 may be initially aligned with the first set of windings 78A as shown in FIG. 4A, then the controller 68 may energize the second set of windings 78B in an alternating manner with the first set of windings 78A (e.g., switching the windings 78A, 78B on/off) to cause the rotor 74 to oscillate back-and-forth between the first and second sets of windings 78A, 78B, and thereby vibrate. Such oscillation being shown by arrow 75. Similarly, the first set of windings 78A may be energized to place the rotor 74 in the alignment shown in FIG. 4A, then the controller 68 may energize the remaining second and third sets of windings 78B, 78C in an alternating manner (e.g., switching the windings 78B, 78C on/off) to cause the rotor 74 to oscillate back-and-forth between the second and third sets of windings 78B, 78C. The frequency with which the rotor 74 oscillates can be controlled by the controller 68 to change the vibration, and thus the characteristic of the feedback FB. Furthermore, in cases where a load is present on the rotor 74, the rotor 74 may move only slightly, e.g., less than 15 degrees, less than 10 degrees, etc. as the windings are being switched on/off as described herein.

Rotor position may be measured by external position sensors, such as Hall-effect sensors and/or optical encoders, or may be determined by back EMF using conventional techniques. The manner in which the sets of windings 78A, 78B, 78C are energized/de-energized may be based on the measured position of the rotor 74 to cause the rotor 74 to oscillate as described, e.g., when the rotor 74 aligns with the second set of windings 78B, then the second set of windings 78B are de-energized and the first set of windings 78A are energized, and vice versa.

Various systems and control techniques to energize the windings 78A, 78B, 78C in a manner to generate sounds are described in International Application Number PCT/CN2015/089691 to Qiu Lan et al., filed on Sep. 16, 2015, published as International Publication Number WO 2017/045144 on Mar. 23, 2017, entitled, "System, Apparatus and Method for Generating Sound," which is hereby incorporated herein by reference.

Vibration of the motor 72 can occur at different predetermined frequencies, durations, and the like to generate different types of feedback FB. Those having ordinary skill in the art will appreciate that audible feedback AF occurs within a range of frequencies which are detectable by the human ear. Moreover, it will be appreciated that vibration of the motor 72 can simultaneously generate both audible feedback AF and haptic feedback HF of different intensities. By way of non-limiting example, feedback FB generated by the motor 72 could be haptic feedback HF realized as vibrations translated to and felt by the user at the input device 64, and also as audible feedback AF realized as a relatively quiet hum or buzzing noise. Conversely, feedback FB generated by the motor 72 could be audible feedback AF realized as a relatively loud tone, and also as haptic feedback HF realized as vibrations translated to but not necessarily felt by the user at the input device 64. In some versions, the motor 72 may comprise an eccentric mass attached to the rotor 74, either directly, or to a motor shaft to which the rotor 74 is attached, such as an eccentric rotating mass vibration motor. The eccentric mass creates an unbalanced force on the motor when it rotates, which translates into vibrations.

As noted above, the controller 68 is disposed in electrical communication with the input device 64 and the actuators 66. To this end, the controller 68 may have one or more microprocessors for processing instructions or for processing an algorithm stored in memory to control operation of the actuators 66 and/or generation of the input signal IS, the feedback signal SF and/or the operate signal SO, such as via the drive circuit 80 as noted above. Additionally or alternatively, the controller 68 may comprise one or more microcontrollers, field programmable gate arrays, systems on a chip, discrete circuitry, and/or other suitable hardware, software, or firmware that is capable of carrying out the operational and feedback functions OF, FF described herein.

The controller 68 may be carried on-board the patient support apparatus 30, such as on the base 34, or may be remotely located. The controller 68 may comprise one or more subcontrollers configured to control all the actuators 66 or one or more subcontrollers for each actuator 66. The controller 68 may communicate with the actuator 66 via wired or wireless connections. The controller 68 may monitor a current state of the components of the patient support apparatus 30, such as with the use of one or more sensors 82, to determine the desired state that the actuator 66 should be placed in, such as based on one or more input signals IS that the controller 68 receives from one or more user input devices 64. The state of the actuator 66 may be a position, a relative position, a pressure, an intensity, a speed, a frequency, an amplitude, a period, an angle, an energization status (e.g., on/off), or any other suitable parameter. The sensors 82 may comprise one or more force sensors (e.g., load cells), timers, temperature sensors, switches, heart monitors, acoustic sensors (e.g., a cough monitor), microphones, breathing monitors, optical sensors, electromagnetic sensors, motion sensors, accelerometers, potentiometers, infrared sensors, ultrasonic sensors, mechanical limit switches, membrane switches, and cameras. Other types of sensors 82 are also contemplated. Some of the sensors 82 may monitor thresholds or discrete point movements. The sensors 82 can be located anywhere on the patient support apparatus 30 or remote from the patient support apparatus 30. For example, the sensors 82 may be located on or in the base 34, the intermediate frame 36, the patient support deck 38, the mattress 42, the side rails 46, 48, 50, 52, the headboard 54, the footboard 56, or other suitable locations.

In one embodiment, one or more sensors 82 may be used to determine a current patient condition. Various current patient conditions can be determined and used to control operation of the patient support apparatus 30. Such patient conditions can comprise current positions of the patient (e.g., the patient is slouched, the patient is off center, the patient is lying supine, the patient is getting ready to exit, the patient is sitting up, etc.). Patient conditions can also comprise physiological conditions (e.g., a patient's heart rate, respiration, temperature, blood pressure, the patient is sleeping, the patient is coughing, skin conditions of the patient, etc.). Patient conditions can also comprise standard patient characteristics (e.g., weight, width, height, pathology, race, etc.). Patient conditions can also comprise patient history (e.g., activity level, movement history, etc.). Patient conditions can be determined by the controller 68 using the sensors 82 and/or by input from the caregiver, patient, or other person, or retrieved from an electronic medical database.

Referring now to FIGS. 1-4, as noted above, the input device 64 is configured to generate an input signal IS communicated to the controller 68 to drive the actuator 66. Those having ordinary skill in the art will appreciate that the input signal IS could be realized in a number of different ways depending on the specific configuration of the input device 64. By way of non-limiting example, the input signal IS could be realized as a variable signal, a digital or analog signal, a waveform, and the like. Thus, as will be appreciated from the subsequent description below, either via the input signal IS directly or by the controller 68, the output signal or waveform used to drive the motor 72 could effect performance of the operational function OF and the feedback function FF in a number of different ways. By way of non-limiting example, a single motor 72 could be driven in such a way that the feedback function FF persists as the operational function OF is carried out.

In the representative embodiments illustrated herein, the patient support apparatus 30 employs a plurality of control panels 84, each of which comprises one or more input devices 64. As is depicted in FIG. 1, control panels 84 are coupled to the patient support apparatus 30 in different predetermined locations, such as on the footboard 56 and one or more of the side rails 46, 48, 50, 52. However, it will be appreciated that one or more of the input devices 64 could be implemented without the use of a discrete control panel 84. By way of non-limiting example, in FIG. 1, the patient support apparatus 30 also employs an input device 64 realized as a foot-pedal to be actuated by the user's foot. Thus, those having ordinary skill in the art will appreciate that the patient support apparatus 30 could employ a number of different input devices 64, of a number of different types and/or configurations, which cooperate to effect control of the patient support apparatus 30. By way of non-limiting example, the patient support apparatus 30 could also employ handheld tethered or wireless remote controls, vocal or gesture controls, and the like. In one embodiment, each input device 64 is configured to generate a respective input signal IS communicated to the controller 68 which, in turn, is configured to perform one of the predetermined operational functions OF, such as movement of portions of the support structure 32 as noted above.

Referring now to FIG. 3B, as noted above, the feedback FB generated by the actuator 66 when performing the feedback function FF is audible feedback AF in one embodiment. Here, the controller 68 is configured to control one or more of the actuators 66 to generate the audible feedback AF in response to the determination of one or more alarm conditions, such where the patient attempts to exit the patient support apparatus 30 without assistance from the caregiver. Such an alarm condition may be determined by the controller 68 via the sensors 82. In one embodiment, the controller 68 is configured to control the actuator 66 to generate audible feedback AF in a plurality of different tones, which may each provide the user with correspondingly different notifications. By way of example, the audible feedback AF may be a first tone corresponding to a low priority alarm, a second tone corresponding to a medium priority alarm, and a third tone corresponding to a high priority alarm, where each respective tone (and, thus, each respective priority alarm) can be differentiated by the user. It will be appreciated that different tones and/or alarm priorities could be used to indicate any suitable type of occurring situation, condition, and the like of the patient support apparatus 30. By way of non-limiting example, audible feedback AF in the first tone for the low priority alarm could indicate that the patient is moving excessively upon the patient support deck 38, audible feedback AF in the second tone for the medium priority alarm could indicate that the patient is about to exit the patient support apparatus 30, and audible feedback AF in the third tone for the high priority alarm could indicate that the patient has exited the patient support apparatus 30.

It will be appreciated that the actuators 66 of the patient support apparatus 30 could be configured to generate the different tones as audible feedback AF in a number of different ways. By way of non-limiting example, the actuators 66A, 66B, 66C could each be configured to perform different feedback functions FF by generating respectively different audible feedback AF: the lift actuator 66A could generate the first tone corresponding to the low priority alarm, the first deck actuator 66B could generate the second tone corresponding to the medium priority alarm, and the second deck actuator 66C could generate the third tone corresponding to the high priority alarm. Conversely, each actuator 66 could be configured to generate a number of tones as audible feedback AF. Thus, it will be appreciated that one, some, or all actuators 66 could generate the same tones at the same time to provide the same audible feedback AF.

The feedback function FF of the actuator 66 can also be used to indicate a status condition to the user. By way of non-limiting example, feedback FB realized as audible feedback AF could be used to verify proper functionality of one or more actuators 66, such as may be advantageously implemented in connection with a diagnostics and/or service mode of the patient support apparatus 30. Here, the controller 68 could be configured to sequentially (or, selectively) control the actuators 66A, 66B, 66C to perform the feedback function FF to generate audible feedback AF in such a way that the user (for example, a technician) could verify proper functionality of each of the actuators 66 of the patient support apparatus 30 and, thus, could differentiate respective status conditions of the actuators 66. Here, the status conditions could be communicated to the user via comparison of audible feedback AF (or, the lack thereof) of each actuator 66 against one another such that inconsistent, irregular, or otherwise unexpected audible feedback AF generation may indicate that one or more actuators 66 should be serviced, replaced, and the like (for example, an overheated motor). In one embodiment, each actuator 66A, 66B, 66C generates different audible feedback AF, either during normal operation or during a service test, distinguishable in such a way (for example, tone or pitch) that the user can self-identify which actuator 66A, 66B, 66C is operating. Thus, deviation from this different audible feedback AF will be readily apparent to the user, either by the lack of generation of audible feedback AF or by a deviation from the expected generation of audible feedback AF.

Referring now to FIG. 3C, as noted above, the feedback FB generated by the actuator 66 when performing the feedback function FF is haptic feedback HF in one embodiment. Here, too, the controller 68 is configured to control one or more of the actuators 66 to generate haptic feedback HF which can be used to indicate a status condition to the user. By way of non-limiting example, haptic feedback HF could be used to verify proper functionality of one or more actuators 66, such as may be advantageously implemented in connection with a diagnostics and/or service mode of the patient support apparatus 30. Here, the controller 68 could be configured to sequentially (or, selectively) control the actuators 66A, 66B, 66C to perform the feedback function FF to generate haptic feedback HF in such a way that the user (for example, a technician) could verify proper functionality of each of the actuators 66 of the patient support apparatus 30 and, thus, could differentiate respective status conditions of the actuators 66. Here, the status conditions could be communicated to the user via comparison of haptic feedback HF (or, the lack thereof) of each actuator 66 against one another such that inconsistent, irregular, or otherwise unexpected haptic feedback HF generation may indicate that one or more actuators 66 should be serviced, replaced, and the like. In one embodiment, each actuator 66A, 66B, 66C generates different haptic feedback HF, either during normal operation or during a service test, distinguishable in such a way (for example, vibration frequency) that the user can self-identify which actuator 66A, 66B, 66C is operating. Thus, deviation from this different haptic feedback HF will be readily apparent to the user, either by the lack of generation of haptic feedback HF or by a deviation from the expected generation of haptic feedback HF. In one embodiment, the controller 68 is configured to generate a plurality of different haptic waveforms, which may be used to perform the feedback function FF by vibrating one or more of the actuators 66 at different frequencies so as to generate correspondingly different haptic feedback HF.

As noted above, the input device 64 and the actuators 66 are each coupled to the support structure 32 in one embodiment. Referring now to FIG. 3D, the control panel 84, the lift actuator 66A, the first deck actuator 66B, and the second deck actuator 66C are each coupled to the support structure 32. In the embodiment illustrated in FIG. 3D (as well as in FIGS. 3A-3C), the control panel 84 comprises a total of six input devices 64, each of which performs a corresponding operational function OF: one for raising the patient support deck 38 via the lift actuator 66A; one for lowering the patient support deck 38 via the lift actuator 66A; one for raising a fowler section of the patient support deck 38 via the first deck actuator 66B; one for lowering the fowler section of the patient support deck 38 via the first deck actuator 66B; one for raising a foot/leg section of the patient support deck 38 via the second deck actuator 66C; and one for lowering the foot/leg section of the patient support deck 38 via the second deck actuator 66C. In the representative embodiment illustrated in FIG. 3D, the controller 68 is configured to drive the second deck actuator 66C to perform the feedback function FF to generate feedback FB realized as haptic feedback HF such that actuation of any one of the six input devices 64 of the control panel 84 causes vibrations to be transmitted from the actuator 66 through the support structure 32 towards the input device 64 to provide the user with tactile, haptic feedback HF.

In the embodiment illustrated in FIG. 3D, the controller 68 drives the second deck actuator 66C alone to perform the feedback function FF to generate haptic feedback HF because the second deck actuator 66C is closest in proximity of the control panel 84 and the input devices 64 in this embodiment. However, those having ordinary skill in the art will appreciate that any one, some, or all of the actuators 66 could be driven by the controller 68 to generate haptic feedback HF realized as vibrations transmitted through the support structure 32 towards the input device 64. Moreover, it will be appreciated that each actuator 66 could generate haptic feedback HF at respectively different frequencies, durations, intensities, and the like, such as may be advantageously used to differentiate input devices 64 arranged in a common control panel 84 from each other, to differentiate different functionality of the input devices 64 in carrying out the operational functions OF, and the like. Moreover, it will be appreciated the controller 68 could be configured such that only one actuator 66 performs the feedback function FF for all actuators 66 of the patient support apparatus 30 (for example, the actuator 66 closest to the input device 64). In one embodiment, one or more of the input devices 64 comprise non-tactile user interfaces, such as conventional touchscreens. However, those having ordinary skill in the art will appreciate that input devices 64 could also be implemented as non-tactile user interfaces of any suitable type.

In some cases, two of the actuators 66 are controlled by the controller 68 to simultaneously perform an operational function OF and a feedback function 66. For example, as the user actuates the input device 64 associated with one of the operational functions OF, e.g., raising the patient support deck 38, the controller 68 generates a corresponding operate signal SO to drive the motor 72 of the lift actuator 66A to raise patient support deck 38. Simultaneously, the controller 68 generates a feedback signal FS to energize the motor 72 of the second deck actuator 66C in a manner that provides a feedback function FF, e.g., haptic feedback HF to the user in the form of vibrations transmitted to the input device 64 being actuated. In this manner, two different motors 72 are simultaneously being energized to perform both operational and feedback functions OF, FF. In other embodiments, the two or more motors 72 can be sequentially energized to perform both operational and feedback functions OF, FF. Likewise, a single motor 72 can be sequentially energized to perform an operational function OF first, and then a feedback function FF, and/or vice versa. Further, the controller 68 may also alternate the operate signal SO and the feedback signal FF in a particular pattern, cycle, etc., to control one or more of the motors 72 to perform the operational function OF and the feedback function FF.

The specific type of haptic feedback HF generated by the actuators 66 could be used to provide the user with a number of different types of tactile feedback FB and, thus, could advantageously afford the patient support apparatus 30 with enhanced functionality in use. By way of illustration, haptic feedback HF could be implemented as a short "burst" of vibration directed towards to the user so as to indicate proper activation of the input device 64. Here, controller 68 could be configured such that a "burst" of vibration haptic feedback HF implemented as the feedback function FF could precede, coincide with, overlap in time with, or be delayed with respect to desired operational function OF. Similarly, the haptic feedback HF could vary or change during performance of the operational function OF. By way of example, the haptic feedback FB could increase or decrease in intensity as the operational function OF is carried out.

In one embodiment, there is a time delay between the activation of the input control 64, the initial generation of the feedback function FF, and the subsequent occurrence of the operational function OF, such as may be implemented to prevent inadvertent activation of the operational function OF where there is unintentional actuation of the input device 64. In one embodiment, there is a time delay between the activation of the input control 64 and the generation of the feedback function FF, which may precede or occur simultaneously with the operational function OF. It will be appreciated that the feedback function FF may persist for all or part of the carrying out of the operational function OF. In one embodiment, there is a first time delay between the activation of the input control 64 and the generation of the feedback function FF, and a second time delay between the generation of the feedback function FF and the occurrence of the operational function OF.

Figure 5:
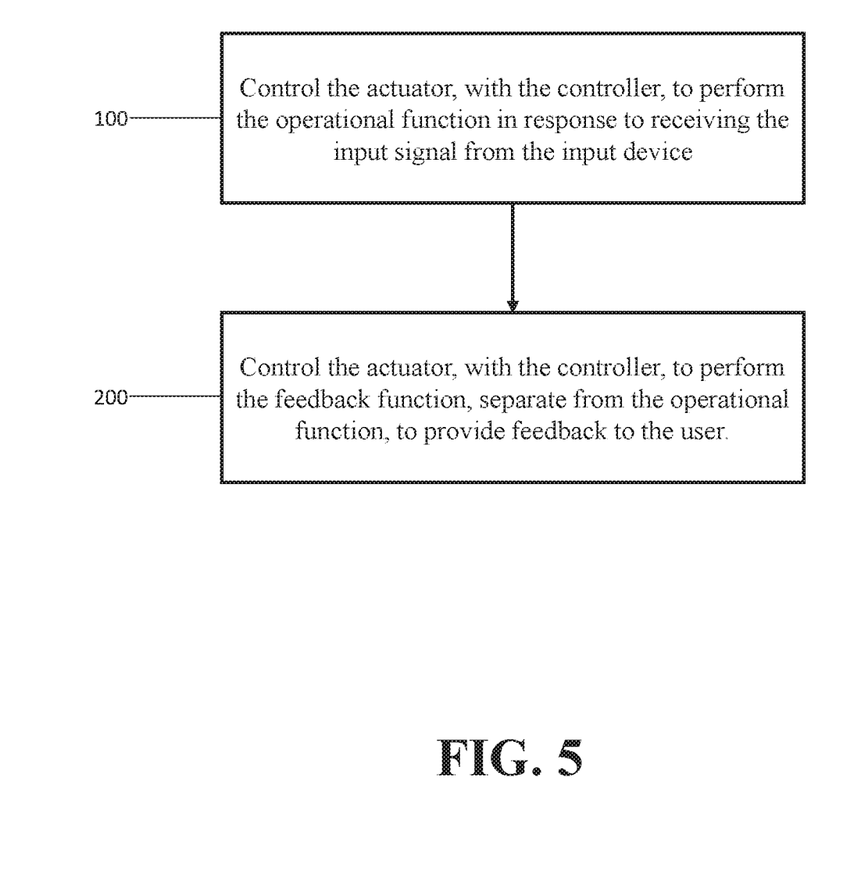
FIG. 5 depicts exemplary steps of a method of operating patient support apparatuses of the disclosure.

Referring to FIG. 5, one method of operating the patient support apparatus 30 is illustrated. In this method, the actuator 66 is controlled with the controller 68 to perform the operational function OF in step 100. As described herein, the controller 68 performs the operational function OF in response to receiving the input signal IS from the input device 64. Further, in this method, the actuator 66 is controlled with the controller 68 to perform the feedback function FF, separate from the operational function FO, in step 200. As described herein, the controller 68 performs the feedback function FF to provide feedback to the user. It will be appreciated that step 100 and 200 could be performed in any suitable way consistent with the description of the patient support apparatus 30 discussed herein. By way of non-limiting example, step 200 could precede step 100, step 100 and step 200 could occur simultaneously or could overlap with each other, and the like.

In this way, the patient support apparatus 30 and method of the present disclosure afford significant opportunities for providing users with feedback FB without necessitating the use of expensive, discrete components such as speakers, motors with eccentric masses, and the like. Specifically, it will be appreciated that actuators 66 configured to perform operational functions OF widely used in connection with patient support apparatuses 30, such as movement and articulation of the patient support deck 38, can also be used to perform feedback functions FF to provide the user with feedback FB. Specifically, the controller 68 can drive one or more of the actuators 66 to generate audible feedback FB without necessitating the use of speakers or other types of annunciators to sound alarms. Similarly, the controller 68 can drive one or more of the actuators 66 to generate haptic feedback HF used to provide the user with tactile feedback FB in the form of vibrations translated to the input device 64, thereby affording opportunities for enhanced control, functionality, and user experience without necessitating the use of additional motors or complex and expensive touchscreen interfaces. Thus, the patient support apparatus 30 can be manufactured in a cost-effective manner while, at the same time, affording opportunities for improved functionality.

In other embodiments, the user interfaces may provide separate tactile feedback, yet the actuators 66 are utilized to provide audible feedback. In further embodiments, speakers may be integrated into one or more of the user interfaces, yet the actuators 66 are provided to generate haptic feedback HF.

It will be further appreciated that the terms "include," "includes," and "including" have the same meaning as the terms "comprise," "comprises," and "comprising."

Several embodiments have been discussed in the foregoing description. However, the embodiments discussed herein are not intended to be exhaustive or limit the invention to any particular form. The terminology which has been used is intended to be in the nature of words of description rather than of limitation. Many modifications and variations are possible in light of the above teachings and the invention may be practiced otherwise than as specifically described.

What is claimed is:

1. A patient support apparatus comprising:
   a support structure comprising a patient support surface;
   an input device to generate an input signal;
   an actuator coupled to said support structure and configured to perform:
      an operational function to move at least a portion of said support structure, and
      a feedback function, separate from said operational function, to provide one or more of audible and haptic feedback to a user; and
   a controller in communication with said actuator and said input device, said controller configured to control said actuator to perform said operational function in response to receiving said input signal from said input device, and said controller configured to control said actuator to perform said feedback function separate from performing said operational function.

2. The patient support apparatus at set forth in claim 1, further comprising a powered device coupled to said support structure and comprising said actuator, and wherein said powered device comprises one or more of a patient centering device, a patient turning device, a patient ingress/egress device, a lift device, a bed length extension device, a bed width extension device, a deck adjustment device, and a drive device.

3. The patient support apparatus at set forth in claim 1, wherein said actuator comprises a motor having a rotor and a stator, said controller being coupled to said motor to apply an output signal to said motor to vibrate said rotor so that said feedback comprises haptic feedback.

4. The patient support apparatus at set forth in claim 3, wherein said support structure comprises a patient support deck, a base, and an intermediate frame interposed between said patient support deck and said base.

5. The patient support apparatus at set forth in claim 1, wherein said actuator is configured to generate vibrations to be transmitted from said actuator through said support structure towards said input device to the user.

6. The patient support apparatus at set forth in claim 3, wherein said controller is configured to generate a plurality of different haptic waveforms by applying different output signals having different parameters to said actuator.

7. The patient support apparatus at set forth in claim 3, wherein said input device is further configured to generate a second input signal associated with a second operational function, and wherein said controller is configured to control said actuator to generate said haptic feedback to the user in response to actuation of said input device by the user to perform said second operational function.

8. The patient support apparatus at set forth in claim 1, wherein said input device comprises a non-tactile user interface and said controller controls said actuator to generate said haptic feedback on said non-tactile user interface.

9. The patient support apparatus at set forth in claim 3, wherein said operational function comprises a first movement function to move said patient support surface of said support structure.

10. The patient support apparatus at set forth in claim 9, further comprising:
    a second input device to generate a second input signal; and
    a second actuator coupled to said support structure and configured to perform a second movement function, different than said first movement function, to move at least another portion of said support structure;
    wherein said controller is in communication with said second actuator and said second input device, said controller being configured to control said second actuator to perform said second movement function in response to receiving said second input signal from said second input device, and said controller being configured to generate said haptic feedback in response to receiving said second input signal.

11. The patient support apparatus at set forth in claim 3, wherein said haptic feedback is configured to indicate a status condition to the user.

12. The patient support apparatus at set forth in claim 11, further comprising a second actuator coupled to said support structure, wherein said haptic feedback is configured to differentiate status conditions of said actuators.

13. The patient support apparatus at set forth in claim 1, wherein said actuator comprises a motor having a rotor and a stator, said controller being coupled to said motor to apply an output signal to said motor to vibrate said rotor so that said feedback comprises audible feedback.

14. The patient support apparatus at set forth in claim 13, wherein said controller is configured to control said actuator to generate said audible feedback in response to one or more alarm conditions.

15. The patient support apparatus at set forth in claim 13, wherein said controller is configured to control said actuator to generate said audible feedback in a plurality of different tones.

16. The patient support apparatus at set forth in claim 15, wherein said plurality of different tones provide different notifications to the user.

17. The patient support apparatus at set forth in claim 16, wherein said plurality of different tones comprise a first tone, a second tone, and a third tone, to indicate to the user different alarm priorities including a low priority alarm, a medium priority alarm, and a high priority alarm.

18. The patient support apparatus at set forth in claim 13, wherein said audible feedback is configured to indicate a status condition to the user.

19. The patient support apparatus at set forth in claim 18, further comprising a second actuator coupled to said support structure, wherein said audible feedback is configured to differentiate status conditions of said actuators.

20. The patient support apparatus at set forth in claim 1, wherein said actuator comprises a motor configured to generate said feedback.

21. The patient support apparatus at set forth in claim 20, wherein said motor comprises a brushless motor.

22. The patient support apparatus at set forth in claim 20, wherein said controller comprises a drive circuit configured to generate a signal to drive said motor and provide said feedback.

23. The patient support apparatus as set forth in claim 22, wherein said signal is a pulse width modulation signal.

24. The patient support apparatus at set forth in claim 20, wherein said motor is configured to generate vibrations to provide said feedback.

25. A method for providing feedback to a user of a patient support apparatus comprising a support structure having a patient support surface, an actuator coupled to the support structure, an input device, and a controller, said method comprising the steps of:

controlling the actuator, with the controller, to perform an operational function in response to receiving an input signal from the input device; and controlling the actuator, with the controller, to perform a feedback function, separate from the operational function, to provide feedback to the user.

* * * * *